United States Patent [19]

Schach

[11] Patent Number: 5,187,295
[45] Date of Patent: Feb. 16, 1993

[54] PROCESS FOR THE PREPARATION OF 2,4-DICHLORO-5-FLUOROBENZONITRILE

[75] Inventor: Thomas Schach, Hofheim am Taunus, Fed. Rep. of Germany

[73] Assignee: Hoechst Aktiengesellschaft, Frankfurt am Main, Fed. Rep. of Germany

[21] Appl. No.: 837,260

[22] Filed: Feb. 14, 1992

[30] Foreign Application Priority Data

Feb. 20, 1991 [DE] Fed. Rep. of Germany ....... 4105187

[51] Int. Cl.$^5$ ............................................ C07C 253/14
[52] U.S. Cl. .................................... 558/343; 558/425
[58] Field of Search ......................................... 558/343

[56] References Cited

U.S. PATENT DOCUMENTS

| | | | |
|---|---|---|---|
| 3,009,942 | 11/1961 | Klein et al. | 558/343 |
| 3,179,691 | 4/1965 | Koopman et al. | 558/343 |
| 3,644,471 | 2/1972 | DiBella | 558/343 |
| 4,528,143 | 7/1985 | Kurono et al. | 558/343 |

OTHER PUBLICATIONS

Chem. Abs. 113:77918q (1989), Shi et al.

*Primary Examiner*—Joseph Paul Brust

[57] ABSTRACT

Process for the preparation of 2,4-dichloro-5-fluorobenzonitrile, by reacting 5-bromo-2,4-dichlorofluorobenzene with about 10 to about 300 mol % of copper(I) cyanide in the presence of about 10 to about 2,000 mol % of a polar aprotic solvent at temperatures from about 100° to about 250° C. to give 2,4-dichloro-5-fluorobenzonitrile.

8 Claims, No Drawings

PROCESS FOR THE PREPARATION OF 2,4-DICHLORO-5-FLUOROBENZONITRILE

DESCRIPTION

The present invention relates to an improved process for the preparation of 2,4-dichloro-5-fluorobenzonitrile by exchange of the bromine atom in 5-bromo-2,4-dichlorofluorobenzene for the cyanide group. The compound mentioned and the 2,4-dichloro-5-fluorobenzoic acid obtainable therefrom by hydrolysis of the nitrile group are important intermediates for the preparation of antibacterial fluoroquinolones.

The preparation of 2,4-dichloro-5-fluorobenzonitrile is disclosed by CN 1,031,074. In the synthesis described there, 2,4-dichloro-5-fluoronitrobenzene is converted into the corresponding amine by reduction with iron (85% yield). By means of diazotization and a subsequent cyano Sandmeyer reaction 2,4-dichloro-5-fluorobenzonitrile is synthesizable from the amine; by means of hydrolysis said nitrile is converted into the corresponding carboxylic acid (70% yield).

Disadvantages of this known process are on the one hand the poor synthesizability of the starting compound used, 2,4-dichloro-5-fluoronitrobenzene, and on the other the moderate yields of the isolated end product, which are below 60%, relative to the 2,4-dichloro-5-fluoronitrobenzene used.

There was therefore a need for an improved process, by means of which the preparation of 2,4-dichloro-5-fluorobenzonitrile, and 2,4-dichloro-5-fluorobenzoic acid from this by hydrolysis of the nitrile group, is made possible in high yields, starting from an easily synthesizable starting compound.

It has now surprisingly been found that 2,4-dichloro-5-fluorobenzonitrile can be prepared in an advantageous manner and in good yields by reacting 5-bromo-2,4-dichlorofluorobenzene with about 10 to about 300 mol % of copper(I) cyanide in the presence of about 10 to about 2,000 mol % of a polar aprotic solvent at temperatures from about 100 to about 250° C. to give 2,4-dichloro-5-fluorobenzonitrile. The resulting nitrile can, after removal of the polar aprotic solvent, be hydrolyzed using the aqueous solution of a metal hydroxide to give 2,4-dichloro-5-fluorobenzoic acid.

The 5-bromo-2,4-dichlorofluorobenzene used here as starting compound is easily synthesizable by bromination of 2,4-dichlorofluorobenzene in 85–90% yield.

With regard to details of the procedure, the following may be stated:

It is expedient to initially introduce the bromo-2,4-dichlorofluorobenzene into the reaction vessel together with the copper(I) cyanide and the polar aprotic solvent, to dissolve this by heating and to bring the suspension to the reaction temperature.

In order to minimize as much as possible the side reactions which occur to a large extent towards the end of the bromine exchange reaction, the copper(I) cyanide is particularly preferably used in amounts of about 80 to about 100 mol %, relative to the 5-bromo-2,4-dichlorofluorobenzene, and the reaction is preferably terminated at conversion rates of 75 to 90%.

The process according to the invention can be carried out in the presence of atmospheric oxygen. The use of a protective gas, such as for example argon or nitrogen, is possible, but only slight differences result from this compared to working without a protective gas atmosphere.

If the 2,4-dichloro-5-fluorobenzonitrile produced is to be isolated, the preferred work-up is carried out by fractional distillation, unreacted starting compound being able to be recycled.

If required, the 2,4-dichloro-5-fluorobenzonitrile obtained according to the invention can be converted, by means of basic hydrolysis using metal hydroxides, into 2,4-dichloro-5-fluorobenzoic acid. The duration of the hydrolysis for this is between about 0.5 and about 3 hours at temperatures from about 80 to about 100° C. For this, the crude product (2,4-dichloro-5-fluorobenzonitrile), freed from solvent, is heated with alkali metal hydroxides or alkaline earth metal hydroxides and, after removal of the copper salts, the product is precipitated from the aqueous phase by acidification using an inorganic acid.

The process according to the invention is illustrated more closely by the following example, without restricting it thereto.

EXAMPLE

In a 500 ml three-necked flask equipped with reflux condenser and vane stirrer, 243.89 g (1 mol) of 5-bromo-2,4-dichlorofluorobenzene, 80.61 g (0.9 mol) of copper(I) cyanide and 70 g (0.81 mol) of dimethylacetamide are initially introduced into the reaction vessel and heated to 150° C. The reaction suspension is maintained for a further 4 to 5 hours at this temperature with vigorous stirring. Subsequently, it is cooled to 40° C. to 50° C. and the precipitated salts are filtered off by suction. The filter cake is washed 3 times each with 50 ml of methylene chloride and the combined organic phases are fractionally distilled together with the mother liquor. In addition to 39.0 g of 5-bromo-2,4-dichlorofluorobenzene, 127.6 g (80.1%) of 2,4-dichloro-5-fluorobenzonitrile are obtained, relative to reacted 5-bromo-2,4-dichlorofluorobenzene, having a purity (GC) >98%.

If the resulting 2,4-dichloro-5-fluorobenzonitrile is to be converted into 2,4-dichloro-5-fluorobenzoic acid, the crude solution, obtained as described above, is freed in vacuo from solvent and unreacted 5-bromo-2,4-dichlorofluorobenzene and heated with 112 g (2.8 mol) of sodium hydroxide in 1,000 g of water for approximately 2 hours at 100° C., until the gas formation is completed. The crude solution is subsequently adjusted to pH 4.5 using concentrated hydrochloric acid, and the precipitate which has separated out is filtered off. The 2,4-dichloro-5-fluorobenzoic acid formed is precipitated by further addition of HCl to pH 2.0, and the precipitate is subsequently filtered off by suction and washed three times each with 50 ml of water. After drying, 126.4 g (72%) of 2,4-dichloro-5-fluorobenzoic acid are obtained having a purity (GC) >99%.

I claim:

1. A process for the preparation of 2,4-dichloro-5-fluorobenzonitrile, which comprises reacting 5-bromo-2,4-dichlorofluorobenzene with about 10 to about 300 mol % of copper(I) cyanide in the presence of about 10 to about 2,000 mol % of a polar aprotic solvent at temperatures from about 100 to about 250° C. to give 2,4-dichloro-5-fluorobenzonitrile.

2. The process as claimed in claim 1, wherein the reaction with copper(I) cyanide is carried out at temperatures from about 130 to about 190° C.

3. The process as claimed in claim 1, wherein the reaction with copper(I) cyanide is carried out in the presence of tetramethylene sulfone, dimethyl sulfoxide, tetramethylene sulfoxide, dimethylacetamide, dimethylformamide or N-methyl-2-pyrrolidone as polar aprotic solvent.

4. The process as claimed in claim 1, wherein about 50 to about 110 mol % of copper(I) cyanide are used for the reaction.

5. The process as claimed in claim 1, wherein the reaction with copper(I) cyanide takes place in the presence of about 50 to about 200 mol % of a polar aprotic solvent.

6. The process as claimed in claim 1, wherein the process is carried out in the presence of a protective gas.

7. The process as claimed in claim 1, wherein the process is carried out in the presence of nitrogen or argon.

8. The process as claimed in claim 1, wherein the process is carried out at atmospheric pressure, reduced pressure or overpressure.

* * * * *